United States Patent [19]

Carr et al.

[11] 4,400,061
[45] Aug. 23, 1983

[54] LIQUID CRYSTAL ESTER COMPOUNDS EXHIBITING A LOW OR NEGATIVE DIELECTRIC ANISOTROPY AND LIQUID CRYSTAL MATERIALS AND DEVICES INCORPORATING SUCH COMPOUNDS

[75] Inventors: Neil Carr, Hull; George W. Gray, Cottingham; Stephen M. Kelly, Hull, all of England

[73] Assignee: Her Majesty's Government of the UK., London, England

[21] Appl. No.: 229,876

[22] Filed: Jan. 30, 1981

[30] Foreign Application Priority Data

Jan. 30, 1980 [GB] United Kingdom ................ 8003131
Jun. 27, 1980 [GB] United Kingdom ................ 8021069

[51] Int. Cl.$^3$ .......................... G02F 1/13; C09K 3/34; C07C 69/74; C07C 69/76; C07C 121/64
[52] U.S. Cl. ............................ 350/350; 252/299.62; 252/299.63; 260/465 D; 560/118
[58] Field of Search ...................... 252/299.62, 299.63; 260/465 D; 560/118; 350/350 R

[56] References Cited

U.S. PATENT DOCUMENTS

| | | | |
|---|---|---|---|
| 4,219,256 | 8/1980 | Gray et al. | 252/299.62 |
| 4,229,315 | 10/1980 | Krause et al. | 252/299.63 |
| 4,237,026 | 12/1980 | Eidenschink et al. | 252/299.63 |
| 4,261,652 | 4/1981 | Gray et al. | 252/299.62 |
| 4,279,770 | 7/1981 | Inukai et al. | 252/299.64 |
| 4,279,771 | 7/1981 | Shionozaki et al. | 252/299.67 |
| 4,290,905 | 9/1981 | Kambe | 252/299.63 |
| 4,293,434 | 10/1981 | Deutscher et al. | 252/299.63 |
| 4,349,452 | 9/1982 | Osman et al. | 252/299.61 |
| 4,357,078 | 11/1982 | Carr et al. | 252/299.62 |

FOREIGN PATENT DOCUMENTS

| | | | |
|---|---|---|---|
| 19665 | 12/1980 | European Pat. Off. | 252/299.63 |
| 23728 | 2/1981 | European Pat. Off. | 252/299.63 |
| 23730 | 2/1981 | European Pat. Off. | 252/299.63 |
| 105701 | 5/1974 | German Democratic Rep. | 252/299.63 |
| 49-95880 | 9/1974 | Japan | 252/299.67 |
| 55-84385 | 6/1980 | Japan | 252/299.67 |
| 56-43386 | 4/1981 | Japan | 252/299.63 |
| 2063287 | 6/1981 | United Kingdom | 252/299.63 |
| 2071131 | 9/1981 | United Kingdom | 252/299.62 |

OTHER PUBLICATIONS

Osman, M. A., et al., Mol. Cryst. Liq. Cryst., vol. 56 (Lett.), pp. 105-109 (1979).
Deutscher, H. J., et al., Advances in Liq. Cryst. Res. and Appl., Bata, L., Pergamon Press, Oxford, pp. 1075-1079 (1980).
Dewar, M. J. S., et al., JACS, vol. 92, No. 6, pp. 1582-1586 (1970).
Gray, G. W., et al., Mol. Cryst. Liq. Cryst., vol. 67, No. 1-4, pp. 1-24 (1981).
Gray, G. W., et al., Mol. Cryst. Liq. Cryst., vol. 75, pp. 95-108, 109-119 (1981).
Gray, G. W., Mol. Cryst. Liq. Cryst., vol. 63, pp. 3-18 (1981).
Constant, J., et al., Mol. Cryst. Liq. Cryst., vol. 70, pp. 105-114 (1981).

*Primary Examiner*—Teddy S. Gron
*Attorney, Agent, or Firm*—Stevens, Davis, Miller & Mosher

[57] ABSTRACT

Novel liquid crystal ester compounds exhibiting a low or negative dielectric anisotropy have a structural formula:

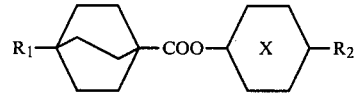

where $R_1$ is an alkyl group, $R_2$ is an alkyl or alkoxy group,

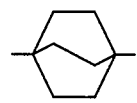

is a 1,4-disubstituted bicyclo(2,2,2) octane ring and

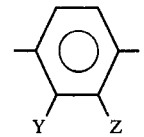

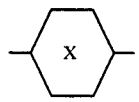

is a 1,4-disubstituted ring selected from the following:
(i) a 1,4-disubstituted bicyclo(2,2,2) octane ring;
(ii) a trans-1,4-disubstituted cyclohexane ring;
(iii) a laterally substituted benzene ring where of the two groups Y and Z one is a halogen or a cyano group and the other is hydrogen or a halogen or a cyano group such that Y is the same as Z.

These esters may be used in a number of known applications including liquid crystal materials for multiplexed twisted nematic devices.

The esters may be made by preparative methods involving known steps.

9 Claims, 7 Drawing Figures

LIQUID CRYSTAL ESTER COMPOUNDS EXHIBITING A LOW OR NEGATIVE DIELECTRIC ANISOTROPY AND LIQUID CRYSTAL MATERIALS AND DEVICES INCORPORATING SUCH COMPOUNDS

The present invention relates to liquid crystal ester compounds exhibiting a low or negative dielectric anisotropy and liquid crystal materials and devices incorporating such compounds.

The use of liquid crystal materials to exhibit electro-optic effects in display devices such as digital calculators or watches is now well known. One of the parameters of a liquid crystal material which is important in relation to electro-optical operation is the dielectric anisotropy ($\Delta\epsilon$) of the material. This is the difference, for a given frequency and temperature between the average dielectric constant measured parallel ($\epsilon_\parallel$) to the molecules of the material, e.g. when aligned together, less the average dielectric constant measured perpendicular ($\epsilon_\perp$) to the molecules.

The sign and magnitude of the dielectric anisotropy of a given liquid crystal material is one of the major parameters which determine the kinds of electro-optic devices in which that material may be used.

For example, materials having a positive dielectric anisotropy, herein referred to as 'positive' materials, eg mixtures of 4-alkyl-or-alkoxy-4'-cyanobiphenyls and a 4''-alkyl-or-alkoxy-4-cyano-p-terphenyl may be used in known twisted nematic effect devices (if nematic) or known cholesteric-to-nematic phase change effect devices (if cholesteric) in which the molecular arrangement is changed from the focal conic to the homeotropic texture.

Materials having a negative dielectric anisotropy herein referred to as 'negative' materials (of suitable resistivity) may be used in known dynamic scattering effect devices (if nematic) or cholesteric memory mode devices (if cholesteric).

Materials having a large negative dielectric anisotropy, as well as those having a low dielectric anisotropy (negative or positive), may also be mixed with those having a positive dielectric anisotropy to produce mixtures whose overall dielectric anisotropy is positive (but reduced in magnitude).

According to the present invention in a first aspect there is provided a novel liquid crystal ester compound exhibiting a low or negative dielectric anisotropy having a structural formula:

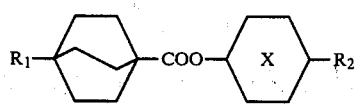
(I)

where $R_1$ is an alkyl group, $R_2$ is an alkyl or alkoxy group

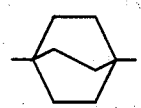

is a 1,4 disubstituted bicyclo(2,2,2)octane ring and

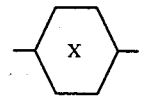

is a 1,4 disubstituted ring selected from the following:
(i) a 1,4 disubstituted bicyclo(2,2,2)octane ring;
(ii) a trans, 1,4 disubstituted cyclohexane ring;
(iii) a laterally substituted benzene ring

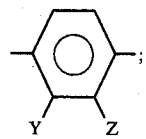

where of the two groups Y and Z one is a halogen or a cyano group and the other is hydrogen or a halogen or a cyano group such that Y is the same as Z.

Thus, where

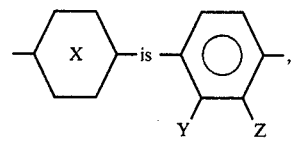

Y is a halogen or cyano group and Z is hydrogen; or Z is a halogen or cyano group and Y is hydrogen; or Z and Y are the same and are halogens or cyano groups. Preferably, Z and/or Y if a halogen is F or Cl.

The groups $R_1$ and $R_2$ preferably contain eighteen or less carbon atoms, desirably twelve or less carbon atoms. These groups may be normal or branched. If branched, one or both may contain a chiral centre in which case the compound may be optically active. If $R_1$ and $R_2$ are normal groups then the compound is nematogenic. Preferably $R_1$ is n-alkyl containing between 1 and 12 carbon atoms inclusive and $R_2$ is n-alkyl containing between 1 and 12 carbon atoms inclusive (if nematogenic) or is $(+)-2$ methylbutyl (if optically active).

By a 'liquid crystal compound' is meant a compound in one of the following two known categories:
(i) Compounds which normally exhibit a liquid crystal phase:
(ii) Compounds which do not normally exhibit a liquid crystal phase but which nevertheless usefully affect some aspect of liquid crystal behaviour when dissolved in other liquid crystal compounds.

Compounds in category (ii) show a 'monotropic' or a 'virtual' liquid crystal to isotropic liquid transition at a temperature below the melting point of their solid phase. The monotropic or virtual transition may be detected respectively by rapid cooling of the liquid phase or by dissolving the compound in a material exhibiting a liquid crystal phase, observing the change in the transition to the isotropic liquid phase of the material by the addition and calculating the virtual transition temperature by extrapolation. Compounds in category (ii) might for example be usefully dissolved in other liquid crystal compounds to extend or vary the liquid crystal temperature ranges of the compounds or to vary the molecular helical pitch (in the case of cholesteric liquid crystals).

The compounds according to formula (I), which are esters of 1-alkyl-4-carboxy bicyclo(2,2,2)octanes and various substituted phenols or analogous bicyclo(2,2,-2)octane or cyclohexane compounds may be prepared by known procedures. In each case the carboxylic acid is preferably converted into its acid chloride by conventional reaction with thionyl chloride. The acid chloride is then reacted with the appropriate phenol or analogous compound under known conditions to give the ester.

One or more compounds according to formula (I) may be used in any of the following applications:

(i) together with a positive nematic material giving an overall positive nematic material for use in twisted nematic effect devices particularly multiplexed devices; an example of such a device is give below;

(ii) either alone (if Δε is large and negative), or together with another nematic material, preferably negative, giving an overall negative material (eg if Δε is small) preferably also with a pleochroic dye, in Freedericksz effect devices in which the molecular arrangement may be changed from the homeotropic texture (OFF state) to the homogeneous texture (ON state); an example of such a device is given below;

(iii) together with a nematic material giving an overall positive nematic material, preferably also with a pleochroic dye, in Freedericksz effect devices in which the molecular arrangement may be changed from the homogeneous texture (ON state) to the homeotropic texture (OFF state) by an electric field;

(iv) together with an optically active material giving an overall negative material which is a cholesteric of suitable resistivity (about $10^9$ ohm-cm), in cholesteric memory mode devices in which the molecular arrangement may be changed from a twisted homogeneous texture (OFF state) to a turbulent scattering focal conic texture (ON state) by an electric field;

(v) together with an optically active material giving an overall negative material which is a cholesteric, preferably together also with a pleochroic dye, in cholesteric-to-nematic phase change effect devices in which the molecular arrangement may be changed from a weakly scattering surface aligned homeotropic texture (OFF state) to a strongly scattering twisted homogeneous texture (ON state) by an electric field;

(vi) together with an optically active material giving an overall positive material which is a cholesteric, preferably together also with a pleochroic dye, in cholesteric-to-nematic phase change effect devices in which the molecular arrangement may be changed from a scattering focal conic texture (OFF state) to a clear homeotropic texture (ON state) by an electric field;

(vii) together with a nematic material giving an overall negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field;

(viii) together with a positive nematic material giving an overall positive nematic material in two frequency switching effect devices in which the dielectric anisotropy of the material may be changed from (at low frequency) positive (OFF state) to negative (ON state) by the application of a high frequency electric field.

The construction and operation of the above devices and the general kinds of material which are suitable for use in them are themselves known.

It will be apparent to those skilled in the art that in the above applications where mixtures are formed these mixtures can have the value and sign of their dielectric anisotropy controlled as required by control of the proportions of the materials blended together to form them.

Where a material is added to one or more compounds according to formula (I) the material may itself be a mixture of 2 or more compounds.

Mixtures may be formed in a known way, e.g. simply by heating the constituent compounds to form an overall isotropic liquid, stirring the liquid and allowing it to cool.

The compounds according to formula (I) may usefully reduce operating voltages in the above applications as well as enhance negativity or reduce positivity of the dielectric anisotropy; this may usefully affect other properties, e.g. multiplexability in twisted nematic effect devices or switching frequency in two-frequency switching effect devices.

According to the present invention in a second aspect there is provided a mixture of liquid crystal compounds including at least one compound according to formula (I) above. Such a mixture may, depending on its selected composition and properties, be used in any one of the applications (i) to (vii) above.

An example of a mixture according to the second aspect which may be used in multiplexed twisted nematic devices is one including, in addition to at least one compound according to formula (I) above, one or more 4'-alkyl- or 4'-alkoxy-4-cyanobiphenyls and one or more of the following compounds:

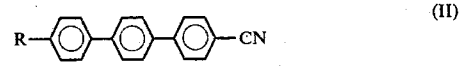
(II)

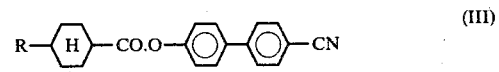
(III)

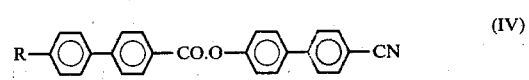
(IV)

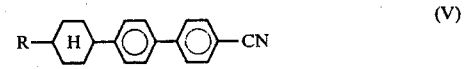
(V)

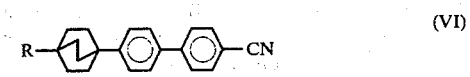
(VI)

(VII)

R=n-alkyl, together with other esters e.g. of the form

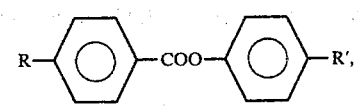

R'=n-alkyl as necessary having a low dielectric anisotropy.

Preferably the 4'-alkyl- or 4'-alkoxy-4-cyanobiphenyls constitute between about 10 and 90% by weight of the mixture and the compounds selected from formulae (II) to (VII) constitute not more than about 20% by weight in total, the remainder being one or more compounds, according to Formula (I) above together with other esters as necessary.

Preferably each 4'-alkyl- or 4'-alkoxy-4-cyanobiphenyl incorporated in the mixture has five or less carbon atoms in its alkoxy or alkyl group. Preferably this number of carbon atoms is odd when the group is an alkoxy group and is even when the group is an alkyl group.

As more general examples, the mixture according to the second aspect may be a compound according to formula (I) above mixed together with one or more compounds in the following known families for use in one or more of the applications given above

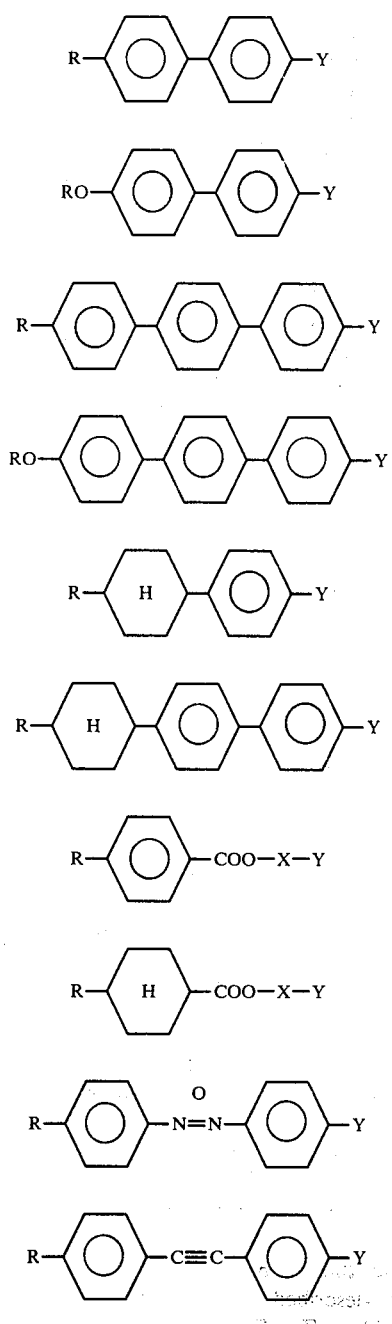

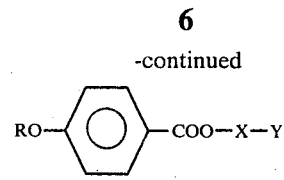

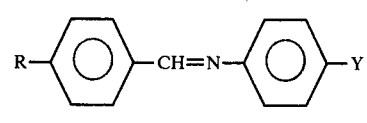

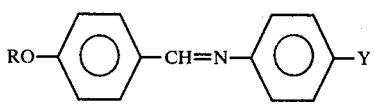

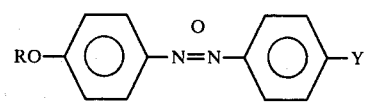

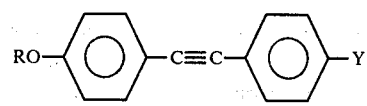

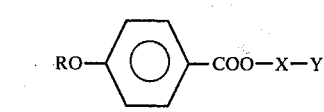

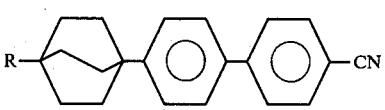

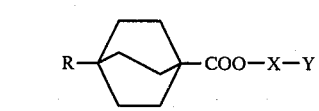

where

is a cyclohexane ring,

is a bicyclo(2,2,2)octane ring, X is a 1,4 phenylene group

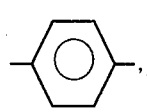

or a 4,4'biphenylyl group

or a 2,6 naphthyl group

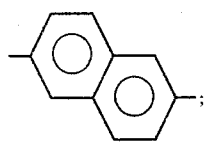

and Y is CN, or $R^1$, or $OR^1$ or $CO.O—X—Y^1$ where $Y^1$ is CN, or R' or OR'; the definition of R' being the same as that of R.

According to the present invention in a third aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterized in that the liquid crystal material consists of or includes a compound according to formula (I) above.

The device according to the third aspect may be a twisted nematic effect device, which may or may not be operated in a multiplexed fashion, a cholesteric-to-nematic phase change effect device, a Freedericksz effect device, a two-frequency switching effect device, a cholesteric memory mode device or a dynamic scattering effect device all constructed in a known manner. The various ways in which compounds according to formula (I) may be used in these devices are outlined above and will be further apparent to those skilled in the art.

Examples of the preparation and properties of compounds according to formula (I) above will now be given.

EXAMPLE 1

The intermediate compounds 1-bromo-4-alkyl substituted bicyclo[2,2,2]octanes are used to prepare intermediate acids used in the preparation of the esters as described below. These bromo compounds may be prepared by the following route:

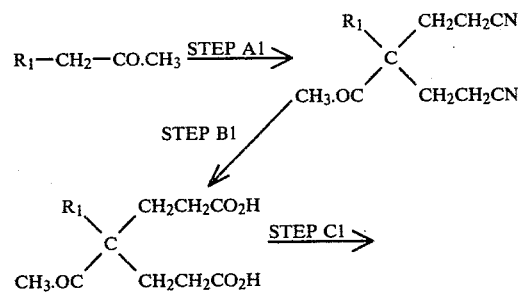

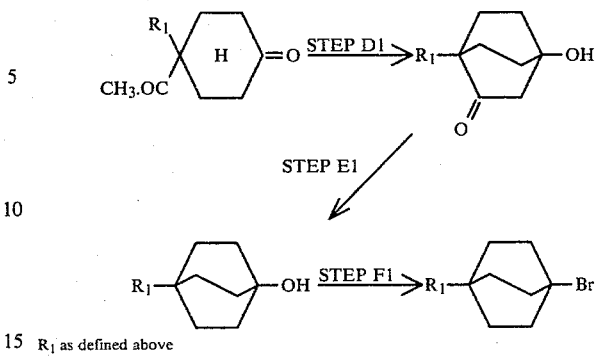

$R_1$ as defined above

STEP A1: The production of 3-acetyl-1,5-dicyano-3 substituted pentane.
STEP B1: The production of 3-acetyl-3-substituted pentane-1,5-dicarboxylic acid.
STEP C1: The production of 4-acetyl-4-substituted cyclohexanone.
STEP D1: The production of 1-hydroxy-4-substituted bicyclo[2.2.2]octan-3-one.
STEP E1: The production of 1-hydroxy-4-substituted bicyclo[2.2.2]octane.
STEP F1: The production of 1-bromo-4-substituted-bicyclo[2.2.2]octane.

All six of these steps may be carried out by methods essentially analogous to those for R=methyl and ethyl described by H. D. Holtz and L. M. Stock in the Preparation of 1-Carboxy-4-Substituted Bicyclo[2,2,2]Octanes, J. Am. Chem. Soc, 86, 5183 (1964).

EXAMPLE 2

This Example describes the preparation of 4-alkyl-2-halogeno phenols which may be the intermediates used to form the esters in Example 11 below. The following route is used:

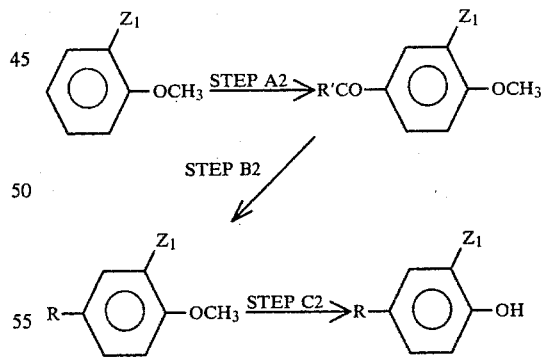

where $Z_1$ is fluoro, chloro, or bromo.
STEP A2: The production of 4-alkanoyl-2-halogeno-anisoles.
STEP B2: The production of 4-alkyl-2-halogeno-anisoles.
STEP C2: The production of 4-alkyl-2-halogeno-phenols.

All three of these steps may be carried out essentially by the steps described in U.K. patent application Ser. No. 8,031,248 for $Z_1$=fluoro.

EXAMPLE 3

This Example describes the preparation of 4-alkyl-3-halogenophenols which may be the intermediates used to form the esters in Example 11 below from the commercially available 2-halogenoanisoles, by the following route:

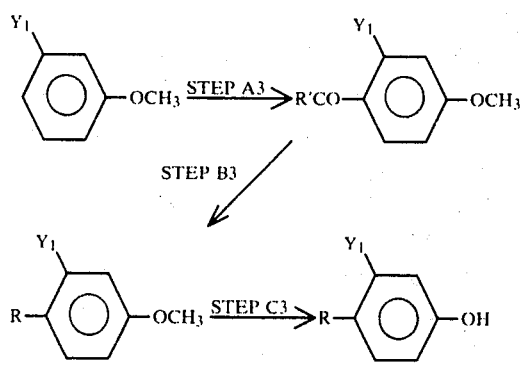

where $Y_1$ is fluoro, chloro, or bromo.

STEP A3: The production of 4-alkanoyl-3-halogenoanisoles.

STEP B3: The production of 4-alkyl-3-halogenoanisoles.

STEP C3: The production of 4-alkyl-3-halogenophenols.

All three of these steps may be carried out essentially by the steps described in U.K. patent application Ser. No. 8,031,248 for $Y_1 = F$.

EXAMPLE 4

This Example describes the preparation of 4-alkyl-2-cyanophenols, which may be the intermediates used in the preparation of the esters in Example 11 below, by the following route:

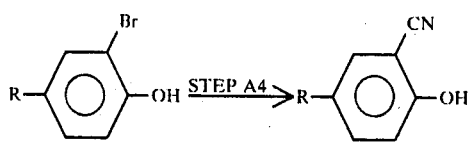

STEP A4: The production of 4-alkyl-2-cyanophenols.

This Step may be carried out by treating the product of Step C2 by a conventional cyanation, e.g. using cuprous cyanide.

EXAMPLE 5

This Example describes the preparation of 4-alkyl-3-cyanophenols, which may be the intermediates used in the preparation of the esters in Example 11 below, by the following route:

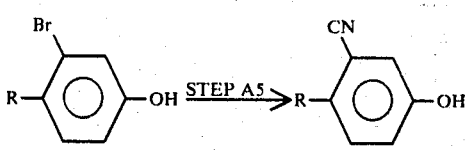

STEP A5: The production of 4-alkyl-3-cyanophenols.

This Step may be carried out by treating the product of Step C3 by a conventional cyanation, e.g. by using cuprous cyanide.

EXAMPLE 6

This Example describes the preparation of trans-1-alkyl-4-cyclohexanols from the corresponding commercially available 4-alkylphenols by the following route:

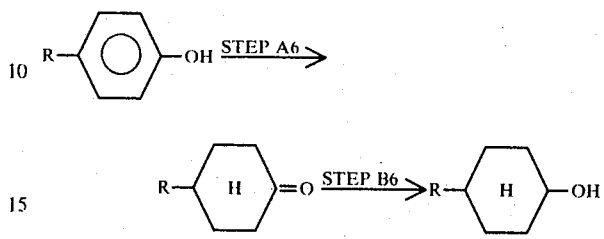

STEP A6: The production of 1-alkyl-4-cyclohexanones.

This Step may be carried out by the method of J. Pines and V. Ipatieff, in JACS, 61, 2728 (1939).

STEP B6: The production of trans-1-alkyl-4-cyclo-hexanols.

This Step may be carried out by the method of E. L. Eliel, R. J. L. Martin and D. Nasyuri, described in Organic Synthesis, 47, 16 (1967).

The trans-1-alkyl-4-cyclohexanols produced in this Example may be the intermediates used in the production of esters as in Example 11 below.

EXAMPLE 7

This Example describes the preparation of various alkoxy phenols which may be used as intermediates in the preparation of liquid crystal esters such as the esters formed in Example 11 below.

The following procedure is used:

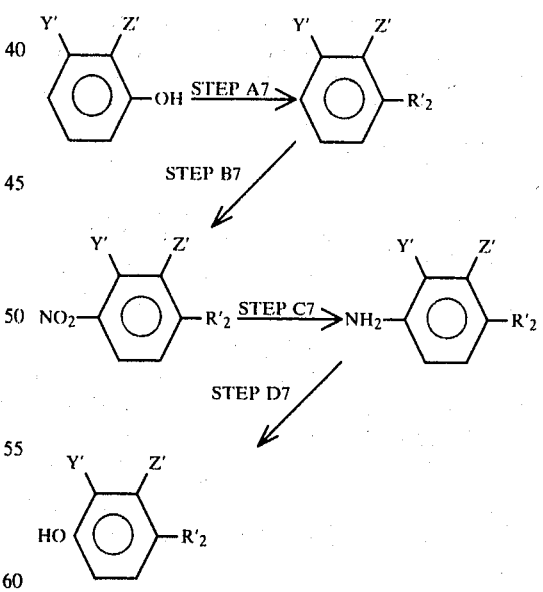

where Y' is F, Cl, Br or CN and Z' is H,
or Y' is H and Z' is F, Cl, Br or CN,
or Y' and Z' are both Cl,
and $R'_2$ is alkoxy.

Steps A7 to D7 are steps which are themselves well known to those skilled in the art of organic chemistry.

The starting compound

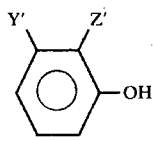

is not commercially available may be obtained from the corresponding anisole

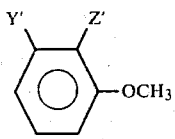

EXAMPLE 8

This Example describes the preparation of 4-alkoxy-2,3 dicyanophenols, which may be used as intermediates in the preparation of the ester described in Example 11 below, by the following route:

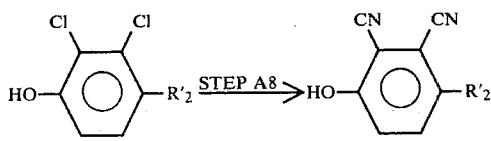

where $R'_2$ = alkoxy.

STEP A8

This Step is carried out by a conventional cyanation treatment, e.g. by using cuprous cyanide. The starting material is the product of Step D7 where Y' and Z' are both Cl.

EXAMPLE 9

1-hydroxy-4-substituted bicyclo-octanes of the form

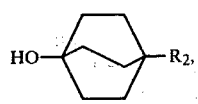

which may be used as intermediates in Example 11 below, may be prepared as in Example 1 above (Steps A1 to E1).

EXAMPLE 10

This Example describes the preparation of 4-alkyl-2,3 dichloro phenol and 4-alkyl-2,3 di-cyanophenol by the following route:

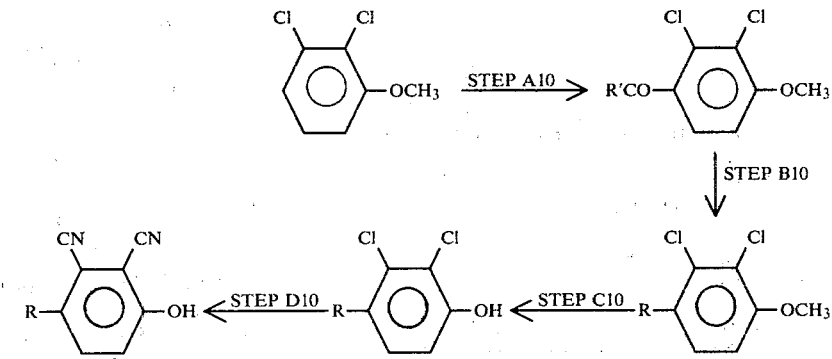

STEP A9: The production of 4-alkanoyl-2,3-dichloro-anisoles.

STEP B9: The production of 4-alkyl-2,3-dichloroanisoles.

STEP C9: The production of 4-alkyl-2,3-dichlorophenols.

STEP D9: The production of 4-alkyl-2,3-dicyanophenols.

Steps A10 to C10 may be carried out in essentially the same way as Steps A2 to C2 respectively and Step D10 may be carried out by a standard cyanation treatment, e.g. by using cuprous cyanide.

The products of Step C10 and D10 may be used as intermediates of the preparation of the esters in Example 11 below.

EXAMPLE 11

The production of ester derivatives of 1-carboxy-4-alkyl substituted bicyclo[2.2.2]octane may be carried out by the following route:

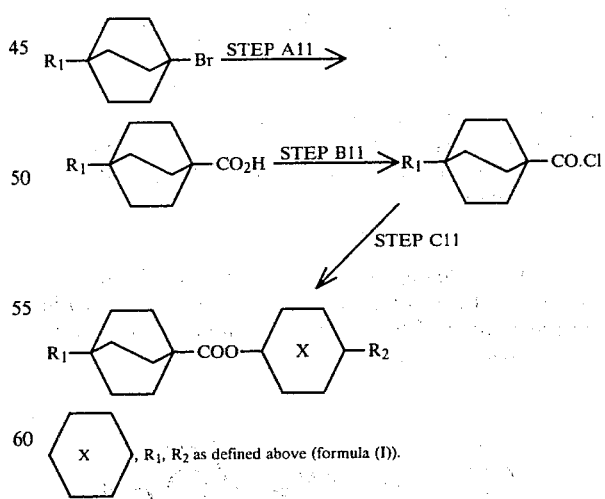

STEP A11: 1-carboxy-4-substituted-bicyclo[2.2.2]octane may be prepared from 1-bromo-4-substituted bicyclo[2.2.2]octane prepared in Example 1, by a modification of the reaction described for R=methyl and ethyl in the paper mentioned above by H. D.

Holtz and L. M. Stock, J. Am. Chem. Soc, 86, 5183 (1964).

STEP B11: The production of 4-substituted 1-bicyclo[2.2.2]octanoyl chloride.

A solution of 1-carboxy-4-substituted bicyclo[2.2.2]octane (0.0018 mole) in dry toluene (10 cm³) is heated under reflux with thionyl chloride (1 cm³) for one hour under anhydrous conditions and then allowed to cool. The mixture is evaporated to dryness under vacuum and then more dry toluene (10 cm³) is added and the resultant solution is again evaporated to dryness under vacuum. The acid chloride residue is used in the next step C5 without further purification.

STEP C11: Ester derivatives of 1-carboxy-4-substituted bicyclo[2.2.2]octanes may be prepared by a suitable modification of the reaction described for the preparation of 1,4-bicyclo[2.2.2]octylene di-4-methoxybicyclo[2.2.2]octane-1-carboxylate by M. J. S. Dewar and R. S. Goldberg in a paper on 'The Role of p-Phenylene Groups in Nematic Liquid Crystals,' J. Am. Chem. Soc, 92, 1582 (1970) using the acid chloride prepared in step B2. This is a conventional esterification between an acid chloride and a substituted phenol or analogous compound. The acid chloride is the product of Step B5 and the phenol or analogous compound may be the product of any one of Steps A5, C2, C3, A4, A5, B6, D7, A8, C10 or D10 as appropriate.

Examples of products of Example 11 are given in Tables 1 to 10 below.

In Tables 1 to 10 below the following symbols are used:

N-I = nematic to isotropic liquid transition temperature
C-I = crystalline solid to isotropic liquid transition temperature
$S_B$-I = smectic B to isotropic liquid transition temperature
C-$S_B$ = crystalline solid to smectic B transition temperature
C-N = crystalline solid to nematic transition temperature
Ch-I = cholesteric to isotropic liquid transition temperature
C-Ch = crystalline solid to cholesteric transition temperature
( ) denotes a monotropic transition temperature
[ ] denotes a virtual transition temperature
(+)—denotes an optically active isomer having a positive optical rotation angle
† denotes a compound which although smectic, to make comparisons possible with other $T_{N-I}$ values, has been used to obtain a virtual N-I value from the properties of a range of mixtures of the compound with a known nematic system (the BDH mixture E7) which strongly represses the smectic B properties.

TABLE 1

Compounds of the formula

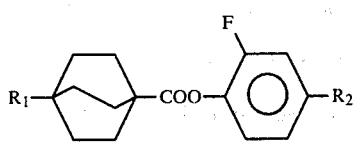

| $R^1$ | $R^2$ | C—N/I in °C. | N—I in °C. |
|---|---|---|---|
| n-C₃H₇ | n-C₃H₇ | | |
| n-C₃H₇ | n-C₄H₉ | 37 | 43 |

TABLE 1-continued

Compounds of the formula

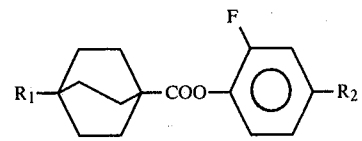

| $R_1$ | $R_2$ | C—N or C—I (°C.) | N—I (°C.) |
|---|---|---|---|
| n-C₃H₇ | n-C₅H₁₁ | 42 | 54.5 |
| n-C₃H₇ | n-C₆H₁₃ | 48 | 45.5 |
| n-C₃H₇ | n-C₇H₁₅ | 51 | (49.5) |
| n-C₄H₉ | n-C₃H₇ | 59 | (46) |
| n-C₄H₉ | n-C₄H₉ | 17 | 32.5 |
| n-C₄H₉ | n-C₅H₁₁ | 23 | 46.5 |
| n-C₄H₉ | n-C₆H₁₃ | 27 | 40 |
| n-C₄H₉ | n-C₇H₁₅ | 30 | 49 |
| n-C₅H₁₁ | n-C₃H₇ | 66.5 | 67 |
| n-C₅H₁₁ | n-C₄H₉ | 27.5 | 48.5 |
| n-C₅H₁₁ | n-C₅H₁₁ | 26 | 62 |
| n-C₅H₁₁ | n-C₆H₁₃ | 20.0 | 55.5 |
| n-C₅H₁₁ | n-C₇H₁₅ | 11.0 | 62.5 |
| n-C₆H₁₃ | n-C₃H₇ | 38 | 57 |
| n-C₆H₁₃ | n-C₄H₉ | 30 | 46 |
| n-C₆H₁₃ | n-C₅H₁₁ | 13 | 48.5 |
| n-C₆H₁₃ | n-C₆H₁₃ | 10 | 47.5 |
| n-C₆H₁₃ | n-C₇H₁₅ | 17 | 54 |

| $R_1$ | $R_2$ | C—N or C—I (°C.) | N—I (°C.) |
|---|---|---|---|
| n-C₃H₇ | n-C₈H₁₇ | 34 | 47.5 |
| n-C₄H₉ | n-C₈H₁₇ | 10.5 | 44 |
| n-C₅H₁₁ | n-C₈H₁₇ | 8.5 | 59 |
| n-C₆H₁₃ | n-C₈H₁₇ | 16 | 50.5 |
| n-C₇H₁₅ | n-C₃H₇ | 60 | 71 |
| n-C₇H₁₅ | n-C₄H₉ | 33 | 53 |
| n-C₇H₁₅ | n-C₅H₁₁ | 29 | 64 |
| n-C₇H₁₅ | n-C₆H₁₃ | 10 | 60 |
| n-C₇H₁₅ | n-C₇H₁₅ | 16 | 61 |
| n-C₇H₁₅ | n-C₈H₁₇ | 7 | 58 |

TABLE 2

Compounds of the formula

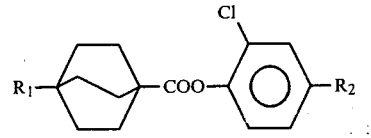

| $R_1$ | $R_2$ | C—N or C—I (°C.) | N—I (°C.) |
|---|---|---|---|
| n-C₃H₇ | n-C₅H₁₁ | 32 | (29.5) |
| n-C₄H₉ | n-C₅H₁₁ | 30 | (19.5) |
| n-C₄H₉ | n-C₆H₁₃ | 27 | (14.5) |
| n-C₄H₉ | n-C₇H₁₅ | 22 | 25.5 |
| n-C₄H₉ | n-C₈H₁₇ | 14 | 22 |
| n-C₅H₁₁ | n-C₅H₁₁ | 33 | 38 |
| n-C₅H₁₁ | n-C₆H₁₃ | 30 | (25) |
| n-C₅H₁₁ | n-C₇H₁₅ | 17 | 40.5 |
| n-C₅H₁₁ | n-C₈H₁₇ | 13 | 35 |
| n-C₆H₁₃ | n-C₅H₁₁ | 25 | 36 |
| n-C₆H₁₃ | n-C₆H₁₃ | 20 | 28 |
| n-C₆H₁₃ | n-C₇H₁₅ | 35.5 | 37.5 |
| n-C₆H₁₃ | n-C₈H₁₇ | 27.5 | 35.5 |

TABLE 3

Optically active compounds of the formula

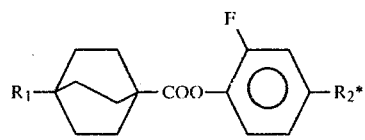

where $R_2{}^* = (+)\text{-}2$ methylbutyl

| $R_1$ | C—Ch or C—I (°C.) | Ch—I |
|---|---|---|
| n-$C_3H_7$ | 36 | (13.5) |
| n-$C_4H_9$ | 27 | [1] |
| n-$C_5H_{11}$ | 43 | (26) |
| n-$C_6H_{13}$ | 31 | (21.5) |
| n-$C_7H_{15}$ | 32.5 | (29.5) |
| n-$C_8H_{17}$ | 22 | 33 |

TABLE 4

Compounds of the formula

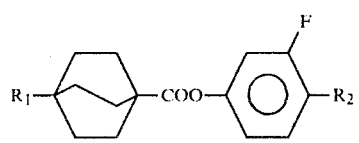

| $R_1$ | $R_2$ | C—N or C—I (°C.) | N—I (°C.) |
|---|---|---|---|
| n-$C_3H_7$ | n-$C_5H_{11}$ | 33 | (24) |
| n-$C_4H_9$ | n-$C_5H_{11}$ | 41 | [14] |
| n-$C_5H_{11}$ | n-$C_5H_{11}$ | 44.5 | (38.5) |
| n-$C_6H_{13}$ | n-$C_5H_{11}$ | 49 | (30) |
| n-$C_7H_{15}$ | n-$C_5H_{11}$ | | |

TABLE 5

Compounds of the formula

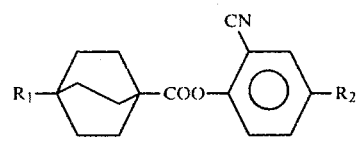

| $R_1$ | $R_2$ | C—N (°C.) | N—I (°C.) |
|---|---|---|---|
| n-$C_5H_{11}$ | n-$C_5H_{11}$ | 27.5 | 29.5 |
| n-$C_6H_{13}$ | n-$C_5H_{11}$ | 26 | 26.5 |
| n-$C_3H_7$ | n-$C_5H_{11}$ | | |
| n-$C_4H_9$ | n-$C_5H_{11}$ | | |
| n-$C_7H_{15}$ | n-$C_5H_{11}$ | | |

TABLE 6

Compounds of the formula

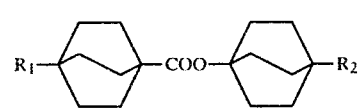

| $R_1$ | $R_2$ | C—$S_B$ (°C.) | $S_B$—I (°C.) | N—I$^+$ (°C.) |
|---|---|---|---|---|
| n-$C_4H_9$ | n-$C_5H_{11}$ | <20 | 184 | [119] |
| n-$C_5H_{11}$ | n-$C_5H_{11}$ | <20 | 191 | [126] |
| n-$C_6H_{13}$ | n-$C_5H_{11}$ | <20 | 190 | [118] |

TABLE 7

Compounds of the formula

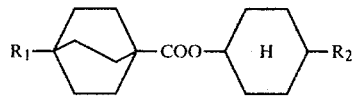

| $R_1$ | $R_2$ | C—$S_B$ (°C.) | $S_B$—I (°C.) | N—I$^+$ (°C.) |
|---|---|---|---|---|
| n-$C_5H_{11}$ | n-$C_5H_{11}$ | 17 | 96 | [92] |

TABLE 8

Compounds of the formula

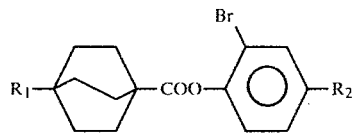

| $R_1$ | $R_2$ | C—N (°C.) | N—I (°C.) |
|---|---|---|---|
| n-$C_5H_{11}$ | n-$C_5H_{11}$ | 14.5 | 27 |

TABLE 9

Compounds of the formula

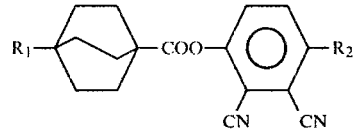

| $R_1$ | $R_2$ |
|---|---|
| n-$C_4H_9$ | n-$C_4H_9$ |
| n-$C_4H_9$ | n-$C_5H_{11}$ |
| n-$C_5H_{11}$ | n-$C_4H_9$ |
| n-$C_5H_{11}$ | n-$C_5H_{11}$ |

TABLE 10

Compounds of the formula

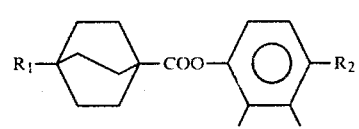

| $R_1$ | $R_2$ |
|---|---|
| n-$C_4H_9$ | n-$C_4H_9$ |
| n-$C_4H_9$ | n-$C_5H_{11}$ |
| n-$C_5H_{11}$ | n-$C_4H_9$ |
| n-$C_5H_{11}$ | n-$C_5H_{11}$ |

Examples of materials and devices embodying the invention will now be described by way of example only with reference to the accompanying drawings wherein.

Figure 1:
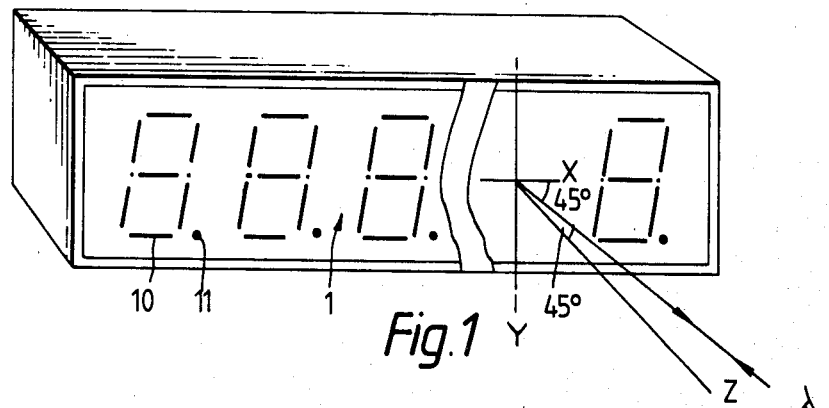
FIG. 1 is a sectional view of a twisted nematic digital display.
Figure 2:
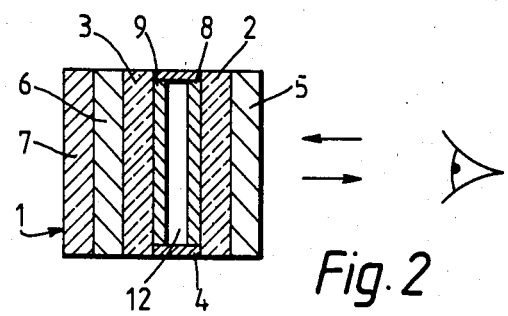
FIG. 2 is a sectional view of the display shown in FIG. 1.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polarizer 5 arranged with its axis of polarization axis horizontal. A reflector 7 is arranged behind the slide 3. A rear polarizer 6 or analyzer is arranged between the slide 3 and reflector 7.

Figure 3:
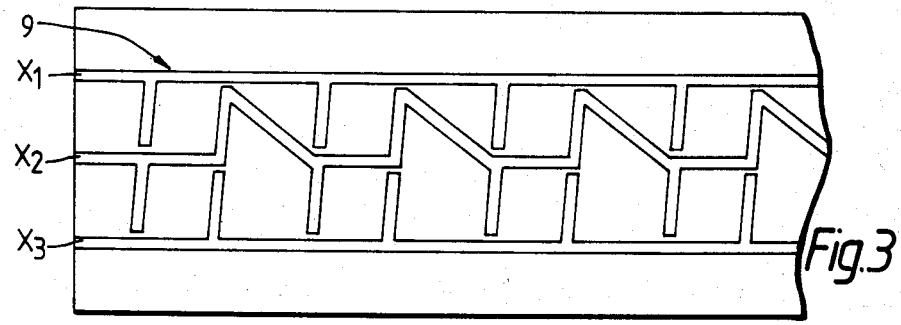
FIG. 3 shows a rear electrode configuration for FIG. 1.
Figure 4:
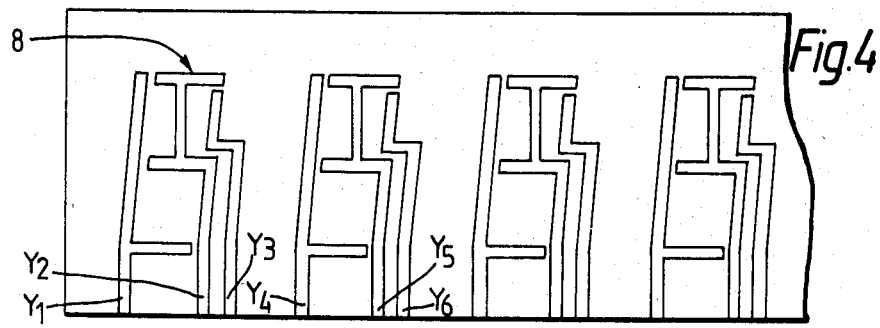
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$.... Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of polyvinyl alcohol (PVA) in water. When dry, the slides are rubbed in a single direction with a soft tissue then assembled with the rubbing directions orthogonal to one another and parallel to the optical axis of the respective adjacent polarizers, i.e. so that the polarizers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polarizer 5, through the cell 1 (whilst having its plane of polarization rotated 90°) through its rear polarizer 6 to the reflector 7 where it is reflected back again to an observer, (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2, 3, i.e. along the axis Z. Thus light at that position does not reach the reflector 7 and does not reflect back to the observer who sees a dark display of one or more bars of a digit 10.

Figure 5:
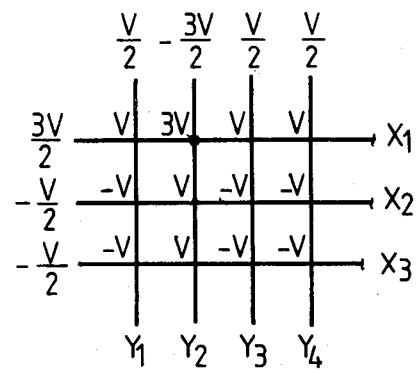
FIGS. 5, 6, 7 show schematic views of the device of FIGS. 1 to 4 with typical addressing voltages.
Figure 6:
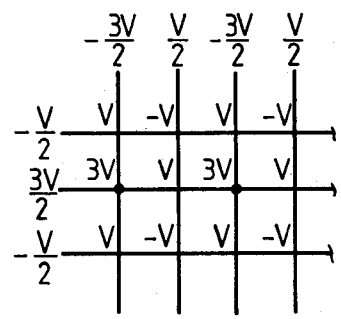
Figure 7:
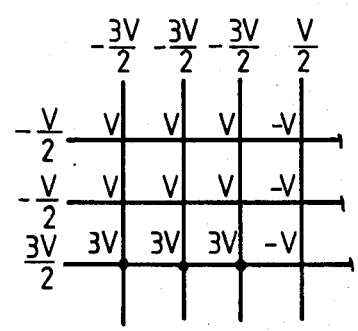

Voltages are applied as follows as shown in FIGS. 5, 6 and 7 for three successive time intervals in a linescan fashion. An electric potential of 3 V/2 is applied to, i.e. scanned down, each x electrode in turn whilst $-V/2$ is applied to the remaining x electrodes. Meanwhile $-3$ V/2 or V/2 is applied to the y electrodes. A coincidence of 3 V/2 and $-3$ V/2 at an intersection results in a voltage 3 V across the liquid crystal layer 12. Elsewhere the voltage is V or $-V$. Thus by applying $-3$ V/2 to appropriate y electrodes as 3 V/2 is scanned down the x electrodes selected intersections are turned ON as indicated by solid circles. The electric voltage V is an ac signal of e.g. 100 Hz square wave, and the sign indicates the phase.

It will be apparent to those skilled in the art that the device shown in FIGS. 1 to 7 is a multiplexed display because the electrodes are shared between ON and OFF intersections or display elements.

A material embodying the invention which is suitable for use as the material 12 in the above device is as in Table 2 as follows (Mixture 1).

TABLE 1

MIXTURE 1

| Compound | Weight percentage |
|---|---|
| $C_2H_5$—⟨○⟩—⟨○⟩—CN | 15 |
| $n$-$C_4H_9$—⟨○⟩—⟨○⟩—CN | 23 |
| $C_2H_5$—⟨H⟩—COO—⟨○⟩—⟨○⟩—CN | 12 |
| $n$-$C_5H_{11}$—⟨H⟩—⟨○⟩—⟨○⟩—CN | 10 |
| $n$-$C_4H_9$—⟨⟩—COO—⟨○⟩—$C_5H_{11}$—$n$ (with F substituent) | 40 |

Alternatively the last mentioned compound may be substituted partially or wholly in the Mixture by one or more of the other fluoro-compounds described above.

Small amounts of a cholesteric material may be added to the nematic material to induce a preferred twist in the molecules in the liquid crystal layer. This and the use of appropriate slide surface treatment removes the problems of display patchiness as taught in U.K. Pat. Ser. Nos. 1,472,247 and 1,478,592. Suitable cholesteric materials are:

C 15 about 0.1 to 0.5% by weight and CB 15 about 0.01% to 0.05% by weight.

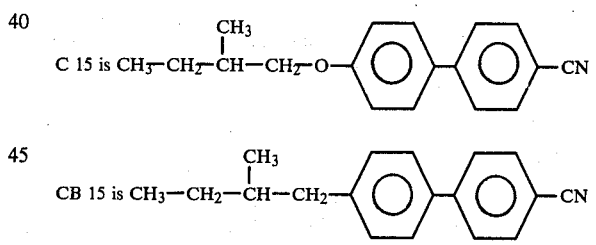

C 15 is $CH_3$—$CH_2$—$\overset{CH_3}{\underset{|}{CH}}$—$CH_2$—O—⟨○⟩—⟨○⟩—CN

CB 15 is $CH_3$—$CH_2$—$\overset{CH_3}{\underset{|}{CH}}$—$CH_2$—⟨○⟩—⟨○⟩—CN

Small amounts of pleochroic dye may be added to enhance the display contrast, e.g. one of the anthraquinone dyes described in U.K. patent application No. 42,810/77.

In another embodiment mixtures embodying the second aspect of the invention may be used in a Freedericksz effect cell. Such a cell may be constructed by sandwiching the liquid crystal material between glass slides having electrode films deposited on their inner surfaces as in the above device. However, in this case the polarizers are not necessary, the glass slide inner surfaces are treated with a coating of lecithin and the liquid crystal material is a negative material whose molecules are aligned in the OFF state perpendicular to the slide substrates (hometropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Freedericksz effect cell made in the above way may incorporate Mixture 2 below, the cell spacing being 10 μm.

TABLE 2
MIXTURE 2

| Compound | Percentage by weight |
|---|---|
| C$_4$H$_9$—⬡—COO—⌬(F)—C$_5$H$_{11}$—n | 47% |
| C$_5$H$_{11}$—⬡—COO—⌬(F)—C$_5$H$_{11}$—n | 47% |
| Compound E<br>C$_2$H$_5$—⬡(H)—COO—⌬(CN,CN)—OOC—⬡(H)—C$_2$H$_5$ | 6% |

The preparation of Compound E is described in U.K. patent application No. 7,934,129.

1.2% by weight of a known pleochroic dye e.g. 1,5-bis-4'-n-butylphenylaminoanthraquinone may be added to Mixture 2 to give a dyed mixture Mixture 2a.

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarizers and surface preparations for homogeneous alignment, e.g. treatment of the glass slide surfaces with SiO, are not used in this case.

If the glass slides are untreated and the liquid crystal material has a positive dielectric anisotropy (Δε) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, e.g. with a coating of lecithin, to give alignment perpendicular to those surfaces, and the liquid crystal material has Δε negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (e.g. 1% by weight of 1,5-bis-4'n-butylphenylamino anthraquinone (in the case where Δε is positive) to the liquid crystal material.

A suitable positive dielectric anisotropy material embodying the invention for use in a phase change effect device is:

TABLE 3
MIXTURE 3

| Material | Percentage by weight |
|---|---|
| Mixture B { C$_2$H$_5$—⌬—⌬—CN 37.5%<br>C$_4$H$_9$—⌬—⌬—CN 37.5%<br>C$_3$H$_7$O—⌬—⌬—CN 25% } | 60% |
| C15 R$_C$O—⌬—⌬—CN (R$_C$ = 2-methyl-butyl) (known) | 10% |
| n-C$_4$H$_9$—⌬(F)—OOC—⬡—C$_5$H$_{11}$—n | 30% |

A suitable negative dielectric anisotropy material embodying the invention for use in a phase change effect device, Mixture 4, is as follows:

TABLE 4
MIXTURE 4

| Compound | Percentage by weight |
|---|---|
| n-C$_5$H$_{11}$—⌬(F)—OOC—⬡—C$_4$H$_9$—n | 45% |
| n-C$_5$H$_{11}$—⌬(F)—OOC—⬡—C$_5$H$_{11}$—n | 46% |
| Compound E<br>C$_2$H$_5$—⬡(H)—COO—⌬(CN,CN)—OOC—⬡(H)—C$_2$H$_5$ | 8% |
| R$_C$—⌬—⌬—COO—⌬—R$_C$<br>(R$_C$ = 2-methylbutyl) | 1% |

In Mixtures 2 and 4 the Compound E may be replaced by one of the di-cyano compounds described above (products of Example 10 where Y and Z are both CN).

In mixtures 1 to 4 the stated fluoro-esters present in the composition may be replaced partially by known unfluorinated esters of the form

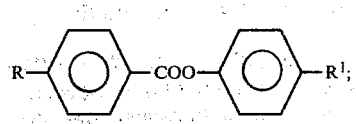

R—⌬—COO—⌬—R$^1$;

-continued

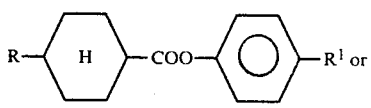

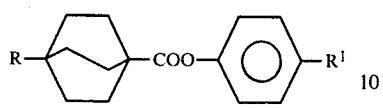

as appropriate (R=alkyl, R¹=alkyl or alkoxy) (see for example the esters used un U.K. patent published application No. 2,031,010A for multiplexed twisted nematic devices).

We claim:

1. A liquid crystal ester compound exhibiting a negative dielectric anisotropy having the structural formula:

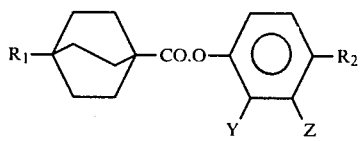

where $R_1$ is an alkyl group; $R_2$ is an alkyl or alkoxy group;

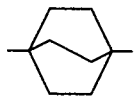

is a 1,4-disubstituted bicyclo(2.2.2) octane ring;

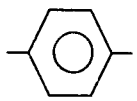

is a 1,4-disubstituted benzene ring;

Y is a group selected from the class consisting of halogen and cyano; and

Z is a group selected from the class consisting of hydrogen, halogen and cyano;

provided that where Z is other than hydrogen it is the same as Y.

2. A compound as claimed in claim 1 and wherein the groups $R_1$ and $R_2$ are n-alkyl groups having between 1 and 12 carbon atoms inclusive.

3. A compound as claimed in claim 2 and wherein Z is the same as Y.

4. A compound as claimed in claim 1 and wherein the group

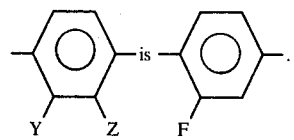

5. A compound as claimed in claim 1 and wherein the group

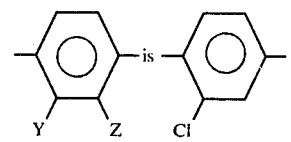

6. A compound as claimed in claim 1 and wherein the group

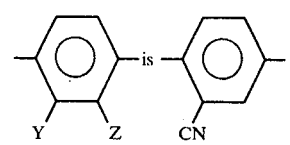

7. A compound as claimed in claim 1 and wherein the group $R_1$ is an n-alkyl group having between 1 and 12 carbon atoms inclusive and the group $R_2$ is $(+)-2$ methylbutyl.

8. A liquid crystal composition comprising a mixture of liquid crystal compounds and wherein the improvement comprises at least one of said compounds being a compound as claimed in claim 1.

9. A liquid crystal electro-optic display comprising two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, and wherein the improvement comprises said liquid crystal material being a liquid crystal composition as claimed in claim 8.

* * * * *